United States Patent
Larsen et al.

(10) Patent No.: US 9,970,152 B2
(45) Date of Patent: May 15, 2018

(54) METHOD FOR FUNCTIONALIZING A SOLID MATERIAL SURFACE WITH SELF ASSEMBLING OR SELF AGGREGATING CYCLODEXTRINS AND PRODUCTS THEREOF

(71) Applicant: Aalborg Universitet, Aalborg Ø (DK)

(72) Inventors: Kim Lambertsen Larsen, Aalborg SØ (DK); Ronnie Nielsen, Aalborg (DK); Karen Østergaard Styrbæk, Fjerritslev (DK)

(73) Assignee: Aalborg Universitet, Aalborg Ø (DK)

(*) Notice: Subject to any disclaimer, the term of this patent is extended or adjusted under 35 U.S.C. 154(b) by 34 days.

(21) Appl. No.: 14/992,932

(22) Filed: Jan. 11, 2016

(65) Prior Publication Data

US 2016/0194820 A1    Jul. 7, 2016

Related U.S. Application Data (62) Division of application No. 13/643,290, filed as application No. PCT/DK2011/050130 on Apr. 20, 2011, now Pat. No. 9,260,299.

(30) Foreign Application Priority Data

Apr. 26, 2010 (DK) .................. 2010 70168

(51) Int. Cl.
| | |
|---|---|
| *C09D 105/16* | (2006.01) |
| *D06M 15/03* | (2006.01) |
| *C08B 37/00* | (2006.01) |
| *C08B 37/16* | (2006.01) |

(Continued)

(52) U.S. Cl.
CPC .............. *D06M 15/03* (2013.01); *B82Y 5/00* (2013.01); *C08B 37/0012* (2013.01); *C08B 37/0015* (2013.01); *C09D 105/16* (2013.01); *A61F 2013/15121* (2013.01); *Y10T 442/2508* (2015.04)

(58) Field of Classification Search
None
See application file for complete search history.

(56) References Cited

U.S. PATENT DOCUMENTS

| | | | | |
|---|---|---|---|---|
| 8,852,895 | B2* | 10/2014 | Darcy | ................. C08B 37/0012 435/97 |
| 2005/0260905 | A1* | 11/2005 | Buschmann | .......... D06M 15/03 442/59 |
| 2009/0227690 | A1 | 9/2009 | Strassburger et al. | |

FOREIGN PATENT DOCUMENTS

| | | | |
|---|---|---|---|
| CN | 101235103 A | 8/2008 | |
| DE | 4035378 A1 * | 5/1992 | .......... D06M 13/005 |
| DE | 10 2007 043 323 A1 | 3/2009 | |

(Continued)

OTHER PUBLICATIONS

Khan et al. (Chem. Rev. 1998, 98, 1977-1996).*

(Continued)

*Primary Examiner* — Vu A Nguyen
(74) *Attorney, Agent, or Firm* — Knobbe, Martens, Olson & Bear, LLP (57) ABSTRACT

The present invention relates to a method for functionalizing a solid material surface with self assembling or self aggregating cyclodextrins, said method comprising the steps of: providing an adsorption solution comprising at least one modified cyclodextrin and at least one solvent; and contacting a solid material surface with the adsorption solution.

9 Claims, 5 Drawing Sheets

(51) Int. Cl.
*B82Y 5/00* (2011.01)
*A61F 13/15* (2006.01)

(56) References Cited

FOREIGN PATENT DOCUMENTS

| | | |
|---|---|---|
| JP | 2009-13547 A | 1/2009 |
| WO | WO 02/077000 A2 | 10/2002 |
| WO | WO 2006/088818 A1 | 8/2006 |
| WO | WO 2009/033635 A2 | 3/2009 |
| WO | WO 2010/114988 A2 | 10/2010 |

OTHER PUBLICATIONS

Machine translation of description of DE 4035378 A1.*
Cristiano, Antonella et al., "Solid-Supported Monolayers and Bilayers of Amphiphilic β-Cyclodextrins" Langmuir, 2007, pp. 8944-8949, vol. 23.

* cited by examiner

METHOD FOR FUNCTIONALIZING A SOLID MATERIAL SURFACE WITH SELF ASSEMBLING OR SELF AGGREGATING CYCLODEXTRINS AND PRODUCTS THEREOF

CROSS REFERENCE TO RELATED APPLICATIONS

This application is a divisional and claims the benefit and priority to U.S. patent application Ser. No. 13/643,290, filed on Oct. 24, 2012, which is a U.S. National Phase Application of PCT International Application Number PCT/DK2011/050130, filed on Apr. 20, 2011, designating the United States of America and published in the English language, which is an International Application of and claims the benefit of priority to Danish Patent Application No. PA 2010 70168, filed on Apr. 26, 2010. The disclosures of the above-referenced applications are hereby expressly incorporated by reference in their entireties.

TECHNICAL FIELD OF THE INVENTION

The present invention relates to a method for functionalizing a solid material surface with self assembling cyclodextrins. In particular, the present invention relates to solid materials coated with a multilayer of self assembling cyclodextrins.

BACKGROUND OF THE INVENTION

Cyclodextrins (CD) are macromolecules which are known for their ability to form inclusion complexes with a wide variety of molecules. A recent area of interest in the field of CD research is the coating of solid materials with CD in order to achieve a functional solid material surface.

The fixation of CD onto a solid material can be achieved in a number of ways. A fixation can range from weak van der Wall interactions to covalent grafting on the solid material. Covalent grafting has attracted considerable attention, whereas the non-covalently grafting has attracted much less attention.

A paper by Cristiano et al. (Langmuir 2007, 23, 8944-8949) discloses a method for the adsorption and spreading of β-cyclodextrin (β-CD) vesicles on hydrophobic and hydrophilic solid material surfaces, which involves a transition from bi-layer vesicles to planar molecular mono-layers or bi-layers. The CD vesicles prefer to interact with hydrophobic and cationic solid material surfaces instead of hydrophilic, non-ionic solid material surfaces. The adsorption of CD vesicles on hydrophobic solid material surfaces results in solid-supported mono-layers of CD in which the alkyl chains of the CD layer cover the hydrophobic solid material surface and leave the hydrophilic part exposed to the aqueous solution. The adsorption of CD vesicles on cationic solid material surfaces results in solid-supported bi-layers of CD. Also in this case, the hydrophilic face of the CD is exposed to the solution. The supported layers function as a supramolecular platform that can bind suitable guest molecules through inclusion in the CD host cavities. However, the limitation to mono- and bi-layers of this method makes it unsuitable for e.g. the textile industry, which needs a thicker CD-layer to obtain a high load of guest molecules.

WO 02/077000 discloses macrocyclic oligosaccharide derivatives, such as cyclodextrines, wherein the subunits making up the macrocycle are modified to enable the macrocycle to self assemble in a suitable solvent to form elongated assemblies comprising a plurality of macrocyclic units. These elongated assemblies have the ability to encapsulate guest molecules such as therapeutic drugs and can be used as hosts for the solubilisation of various compounds. However, a method for grafting the macrocyclic oligosaccharide derivatives onto solid material surfaces is not disclosed.

Several methods for the modification of surfaces with cyclodextrins have been presented in previous art, but only a few aims at creating multiple layers of cyclodextrin with subsequently larger capacity compared to a mono-layer. Multiple layers can be achieved by physical entrapment of cyclodextrins in a polymer matrix covering the surface, as disclosed in WO2009/033635, or by forming a physically immobilized polymer around a e.g. fabric fiber from cyclodextrins by use of either reactive cyclodextrin derivatives (JP2009013547) or by use of chemical cross-linking. Both approaches require time consuming processing and the use of chemical reactants and are as such not suitable for large scale production or coating of surfaces.

Hence, a method for non-covalent grafting onto solid material surfaces would be advantageous.

SUMMARY OF THE INVENTION

The present invention deals with a physical adsorption on a surface of amphiphilic CD which bypasses the need for chemical reaction and offers a range of advantages.

Accordingly, one aspect of the present invention relates to a method for functionalizing a solid material surface with self assembling cyclodextrins, said method comprising the steps of:

a) providing an adsorption solution comprising at least one modified cyclodextrin and at least two solvents;

b) contacting a solid material surface with the adsorption solution;

c) optionally drying the functionalized solid material surface;

characterized in that at least one of the hydroxyl groups (—OH) of said cyclodextrin is modified to —O—$(CO)_n$R, wherein R is a straight or branched aliphatic chain of 1-50 carbons, such as 2-20 carbons, preferably 4-12 carbons, such as 4-8 carbons, and n is an integer from 0 to 1, wherein at least one solvent is polar.

Another aspect of the invention concerns a functionalized solid material obtainable by the method according to the invention.

Another aspect of the invention relates to a functionalized solid material, characterized in that the surface of the solid material contains at least 0.01 $g/m^2$ of one or more modified cyclodextrins, wherein at least one of the hydroxyl groups (—OH) of said cyclodextrin is modified to —O—$(CO)_n$R, wherein R is a straight or branched aliphatic chain of 1-50 carbons, such as 2-20 carbons, preferably 4-12 carbons, such as 4-8 carbons, and n is an integer from 0 to 1.

Yet another aspect of the present invention is to provide an adsorption solution comprising at least one modified cyclodextrin and at least two solvents, characterized in that at least one of the hydroxyl groups (—OH) of the cyclodextrin is modified to —O—$(CO)_n$R, wherein R is a straight or branched aliphatic chain of 1-50 carbons, and n is an integer from 0 to 1, wherein at least one solvent is polar.

Still another aspect of the present invention is to provide a modified cyclodextrin, wherein at least one of the hydroxyl groups (—OH) of the cyclodextrin is modified to —O—$(CO)_n$R, R is a straight or branched aliphatic chain of 1-50 carbons, such as 2-20 carbons, preferably 4-12 carbons, such as 4-8 carbons, and n is an integer from 0 to 1, and said modified cyclodextrin is substantially free of the corresponding unmodified cyclodextrin.

The present invention will now be described in more detail in the following.

DETAILED DESCRIPTION OF THE INVENTION

As mentioned, it is considered useful for e.g. the textile industry to obtain thicker CD-layers on textile surfaces to obtain higher loads of guest molecules. Therefore, it is of interest to increase the thickness of the produced CD-layers on textiles and on solid material surfaces in general. Thus, the present invention provides a method for obtaining a CD-multi-layer on a solid material surface.

In the present context, the term "solid material surface" relates to any surface of a solid material, i.e. a material being in its solid state. Examples of solid materials are: Plastics, wood, glass, ceramics, textiles, metals and paper.

The ability to form complexes with guest molecules is the defining property of the CD. The inclusion complexes vary from inclusion of small molecules e.g. benzene to large macromolecular structures, e.g. proteins. With larger macromolecular structures, the CD can only form an inclusion complex with a small part of the structure, such as a hydrophobic group which is able to sterically fit into the cavity.

The terms "cyclodextrin" and "CD" are used interchangeably throughout this application. The CD is made up of ring bound 1,4 α-linked glucopyranose units. The number of glucopyranose determines the type of cyclodextrin, with the most common having 6, 7 or 8 units called α-, β- and γ-CD, respectively.

Though their structure seems similar except for the size, the three different CD have different properties. A small overview of their properties is presented in Table 1.

TABLE 1

The properties of α, β and γ CD.

| Cyclodextrin | $M_w$ [g/mol] | Outer diameter [nm] | Cavity diameter [nm] | | Solubility [g/kg $H_2O$] | Hydrate $H_2O$ | |
|---|---|---|---|---|---|---|---|
| | | | Inner rim | Outer rim | | cavity | external |
| α CD | 972 | 1.52 | 0.45 | 0.53 | 129.5 | 2.0 | 4.4 |
| β CD | 1134 | 1.66 | 0.60 | 0.65 | 18.4 | 6.0 | 3.6 |
| γ CD | 1296 | 1.77 | 0.75 | 0.85 | 249.2 | 8.8 | 5.4 |

As seen from Table 1, the different CD have varying properties with the most remarkable being the different solubility and their number of hydration $H_2O$. The different properties cannot be explained from size alone as the size goes in the order of α, β and then γ CD whereas the solubility goes β, α and then γ CD. The explanation for the different solubilities is found in the hydroxyl groups present in the CD and their special arrangement. The narrow end is composed of the C6 primary hydroxyl groups of the individual glucopyranose molecules, which have free rotation and thereby result in the formation of the narrow end. The narrow end is denoted the Primary end. The wider end is composed of the secondary hydroxyl groups of the individual glucopyranose molecules, which means that there are twice as many hydroxyl groups in the wider end. The wide end is called the Secondary end. The inside of the CD cavity of all three types of CD is more hydrophobic than water despite the molecule having a very large number of hydroxyl groups. The hydrophobicity comes from the cyclic nature of the CD where the hydroxyl groups are placed on the "rim" of the CD with the more hydrophobic hydrogen in the centre of the CD.

In a preferred embodiment of the present invention, the modified CD is a modified β-CD.

The inventors have found a method to form multi-layers of self assembling cyclodextrins on a solid material surface by controlling the components of an adsorption solution.

In the present context, the term "self assembling cyclodextrins" relates to cyclodextrins which undergo spontaneous assembling into ordered nanostructures.

In the present context, the term "self aggregating cyclodextrins" relates to cyclodextrins which undergo spontaneous assembling into non-ordered/disorganized nanostructures.

In the present context, the term "multi-layer" relates to layers of a factor more than two, such as a tri-layer or more, not to include mono- or bi-layers.

In the present context, the term "polar" refers to a separation of electric charge leading to a molecule having an electric dipole.

In the present context, the term "textile surface" relates to a surface formed from a flexible material consisting of a network of natural or artificial fibres. The network can be both woven and non-woven.

In one aspect of the method of the present invention, the self assembling cyclodextrin is dissolved in a first solvent. One or more additional solvents are then added to form an adsorption solution/suspension.

In another aspect, the self assembling and/or self aggregating cyclodextrin cyclodextrin is dissolved in at least one solvent to form an adsorption solution/suspension.

The inventors have shown that the thickest coating layer is achieved when the adsorption solution comprises micelles or aggregates of self assembling cyclodextrin. Support is found in the experimental section, where little coating is achieved when the adsorption solution is transparent, although the coating is 3-4 times higher than the coating achieved with native β-CD. When dissolving the modified self assembling β-CD in ethanol first and then adding water until a solvent composition from 5 to 35 v/v % (EtOH/water) is reached, the solution obtained is opaque. Additionally, within the before-mentioned concentration range, the largest coating percent is achieved. It is expected that the opaque solution is modified self assembling β-CD in the form of micelles or aggregates.

In a preferred embodiment, the addition of the one or more additional solvents results in the formation of micelles or aggregates of the self assembling cyclodextrin in said adsorption solution. Without being bound by any particular theory, it is thought that the formed micelles or aggregates are thermodynamically unstable, and that this is the driving force for adsorption of the self assembling cyclodextrin onto a solid material surface. The more unstable the suspension, the larger the driving force for adsorption onto a solid material surface. Thus, it is speculated that an unstable adsorption solution is optimal for coating.

The ability of a CD to form micelles or aggregates can be controlled by chemical modification of the CD. This can be done by converting one or more hydroxyl groups into less hydrophilic groups, such as aliphatic ethers or esters with a straight or branched aliphatic chain of 1-50 carbons, such as 2-20 carbons, preferably 4-12 carbons, such as 4-10, 4-9, or 4-8 carbons.

The present invention relates to a method for functionalizing a solid material surface with self assembling cyclodextrins, said method comprising the steps of:
a) providing an adsorption solution comprising at least one modified self assembling cyclodextrin and at least two solvents;
b) contacting a solid material surface with the adsorption solution;
c) optionally drying the functionalized solid material surface;
characterized in that at least one of the hydroxyl groups (—OH) of said cyclodextrin is modified to —O—$(CO)_n$R, wherein R is a straight or branched aliphatic chain of 1-50 carbons, such as 2-20 carbons, preferably 4-12 carbons, such as 4-8 carbons, and n is an integer from 0 to 1, wherein at least one solvent is polar. Optionally, the chains may comprise halogens, alcohols, ethers, carboxylic acids or other functional groups.

Another aspect of the present invention relates to a method for functionalizing a solid material surface with self assembling cyclodextrins, said method comprising the steps of:
a) providing an adsorption solution comprising at least one modified self assembling cyclodextrin and at least two solvents;
b) contacting a solid material surface with the adsorption solution;
c) optionally drying the functionalized solid material surface;
characterized in that at least one of the hydroxyl groups (—OH) of the cyclodextrin is modified to —O—$(NH)_n$R, wherein R is a straight or branched aliphatic chain of 1-50 carbons, and n is an integer from 0 to 1, wherein at least one solvent is polar.

Yet another aspect of the present invention relates to a method for functionalizing a solid material surface with self assembling or self aggregating cyclodextrins, said method comprising the steps of:
a) providing an adsorption solution comprising at least one modified self assembling or self aggregating cyclodextrin and at least two solvents;
b) contacting a solid material surface with the adsorption solution;
c) optionally drying the functionalized solid material surface;
or
a) providing an adsorption solution comprising at least one modified self assembling or self aggregating cyclodextrin and at least one solvent;
b) contacting a solid material surface with the adsorption solution;
c) optionally drying the functionalized solid material surface;
d) optionally contacting the functionalized solid material surface with at least one solvent;
e) provided the use of step d), optionally drying the functionalized solid material surface;
wherein that at least one of the hydroxyl groups (—OH) of said cyclodextrin is modified to —O—$(CO)_n$R$^1$, —NR$^1$R$^2$, —SR$^1$, —N—COR$^1$, or —O—$(CO)_n$OR$^1$;
wherein R$^1$, R$^2$ are independently of one another being selected from hydrogen, alkyl, alkenyl, alkynyl, aryl, and heteroaryl;
R$^1$ and R$^2$, optionally linked with a bridge member Y$_n$, thereby forming one or more rings. Y$_n$ being a bond or a C1-12 alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, S(O)$_{1-2}$ or carbonyl, and wherein n is an integer between 1 and 12.

Yet another aspect of the present invention relates to a method for functionalizing a solid material surface with self assembling or self aggregating cyclodextrins, said method comprising the steps of:
a) providing an adsorption solution comprising at least one modified self assembling or self aggregating cyclodextrin and at least one solvent;
b) contacting a solid material surface with the adsorption solution;
c) optionally drying the functionalized solid material surface;
d) optionally contacting the functionalized solid material surface with at least one solvent;
e) provided the use of step d), optionally drying the functionalized solid material surface;
wherein that at least one of the hydroxyl groups (—OH) of said cyclodextrin is modified to —O—$(CO)_n$R$^1$, —NR$^1$R$^2$, —SR$^1$, —N—COR$^1$, or —O—$(CO)_n$OR$^1$;
wherein R$^1$, R$^2$ are independently of one another being selected from hydrogen, alkyl, alkenyl, alkynyl, aryl, and heteroaryl;
R$^1$ and R$^2$, optionally linked with a bridge member Y$_n$, thereby forming one or more rings. Y$_n$ being a bond or a C1-12 alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, S(O)$_{1-2}$ or carbonyl, and wherein n is an integer between 1 and 12.

In a preferred embodiment, the purpose of R is to promote self assembling and formation of micelles or aggregates.

In a preferred embodiment, the purpose of R$^1$ and R$^2$ is to provide self-assembling or self-aggregating layers of said cyclodextrin on a surface.

In one embodiment of the present invention, the one solvent of the at least two solvents in the adsorption solution is present to lower the polarity of the solvent system in order to promote the formation of micelles or aggregates of the self assembling cyclodextrin in said adsorption solution.

In a specific embodiment of the present invention, the Snyder polarity index (P') of the solvent system in the adsorption solution is decreased by 2 to 35% upon mixing the solvent having the highest individual Snyder polarity index with the one or more additional solvents, such as decreased by 2 to 20% or decreased by 21 to 35%, e.g. decreased by 5 to 15% or decreased by 25 to 30%.

In another embodiment of the present invention, the Snyder polarity index (P') of the solvent system in the adsorption solution is decreased by 2 to 85% upon mixing the solvent having the highest individual Snyder polarity index with the one or more additional solvents, such as decreased by 5 to 70% or decreased by to 65%, e.g. decreased by 15 to 60% or decreased by 35 to 50%.

In the present context the term "Snyder polarity index" relates to the index defined by Snyder in Journal of Chromatography, 92 (1974) 223-230. The Snyder polarity index (P') of the solvent system is calculated by the following equation:

$$P'=a_A(P'_A)+b_B(P'_B)+c_C(P'_C);$$

wherein the letters a-c refer to the solvent volume fractions of the solvents A-C, and ($P'_{A-C}$) refer to the Snyder polarity index of the individual solvents A-C. The equation is not limited to three solvents.

Example 1

$$P'(45\% \text{ (vol/vol) ethanol in water})=a_{water}(P'_{Water})+b_{Ethanol}(P'_{Ethanol})=0.55*(9)+0.45*(5.2)=7.29;$$

Example 2

$$P'(20\% \text{ (vol/vol) ethanol in water})=a_{water}(P'_{Water})+b_{Ethanol}(P'_{Ethanol})=0.80*(9)+0.20*(5.2)=8.24;$$

In yet another embodiment of the present invention, the Snyder polarity index (P') of the solvent system in the adsorption solution is less than 9 in order to promote the formation of micelles or aggregates of the self assembling cyclodextrin in said adsorption solution, such as in the range of 0-8.9, e.g. 0-8.5, such as in the range of 0-7.9, e.g. 0.5-7.5, such as in the range of 1-6.9, e.g. 1.5-6.5, such as in the range of 2-5.9, e.g. 2.5-5.5, such as in the range of 3.5-4.9, e.g. 4.

The hydrophilic-lipophilic balance (HLB) of the self assembling or self aggregating cyclodextrin of the present invention can be measured by a method described by Griffin in 1954. It is a measure of the degree to which self assembling or self aggregating cyclodextrin is hydrophilic or lipophilic, determined by calculating values for the different regions of the molecule.

Griffin's method as described in 1954 works as follows:

$$HLB=20*Mh/M$$

where Mh is the molecular mass of the hydrophilic portion of the Molecule, and M is the molecular mass of the whole molecule, giving a result on an arbitrary scale of 0 to 20. An HLB value of 0 corresponds to a completely hydrophobic molecule, and a value of 20 would correspond to a molecule made up completely of hydrophilic components.

In the present context, the unmodified cyclodextrin (α-, β- and γ-CD), i.e. a cyclodextrin without any substitutions on the hydroxyl groups, is considered as the hydrophilic portion.

In one embodiment of the present invention, the hydrophilic-lipophilic balance (HLB) of the at least one modified self assembling or self aggregating cyclodextrin is in the range of 3-18, such as in the range of 4-15, e.g. 5-13, such as in the range of 6-11, e.g. 7-9.

Example 1

C16 unbranched chain substituted β-CD coupled with an ester bond (—O—(CO)$C_{15}H_{31}$) (14 chains on the secondary side) gives: 20×896/4472=4.0.

As previously described, the molecular weight of unmodified β-CD is 1134. When substituting the β-CD with e.g. 14 C16 unbranched chains as above, the hydrophilic portion is subtracted the 14 hydroxyl groups. Hence the molecular weight of the hydrophilic portion is 1134−(14*17.01)=896. The molecular weight of an unbranched C16 chain plus the two oxygens from the ester bond (—O—(CO)$C_{15}H_{31}$) is 255.41. Hence the molecular weight/mass of the whole molecule is 896+(14*255.41)=4472.

Example 2

C20 unbranched chain substituted β-CD coupled with an ester bond (—O—(Co)$C_{19}H_{39}$) (14 chains on the secondary side) gives: 20×896/5257=3.4.

In another embodiment of the present invention, the adsorption solution comprises a mixture of modified cyclodextrins.

In still another embodiment of the present invention, the solid material surface is a textile surface. In a specific embodiment, the textile surface is selected from the group consisting of: a nylon surface, a polysaccharide surface, a polyethylene surface, and a polypropylene surface. In another embodiment, the solid material surface is selected from the group consisting of a silica oxide surface, a polymer surface, a ceramic surface, a wood surface and a metal surface, or mixtures thereof. In a presently preferred embodiment, the solid material surface is a polypropylene (PP) surface. The terms "polypropylene" and "PP" are used interchangeably herein.

In still another embodiment of the present invention, the solid material surface is hydrophobic.

In another embodiment of the present invention, the solid material surface is hydrophilic.

In another embodiment of the present invention, the adsorption solution is transparent.

In the present context, the term "transparent" refers to a state where turbidity is 500 Nephelometric Turbidity Units (NTU) or less by a turbidimeter/nephelometer (e.g. TN-100, manufactured by Eutech Instruments).

In the present context, the term "turbidity" refers to the cloudiness or haziness of the adsorption solution caused by individual particles (e.g. suspended cyclodextrin or guest molecules). The measurement of turbidity is a key test of e.g. water quality. The adsorption solution can contain suspended solid matter consisting of particles of many different sizes.

In a specific embodiment, when the transparent adsorption solution has been applied to the solid material surface, there will be a selective evaporation of the solvents until the Snyder polarity index (P') of the solvent system in the adsorption solution is suitable for the formation of micelles or aggregates of the self assembling cyclodextrin.

In another embodiment of the present invention, the self assembling cyclodextrins is partly dissolved in the adsorption solution, such as 99% dissolved, such as 0.5-99% dissolved, e.g. 95% dissolved, such as 5-80% dissolved, e.g. 75% dissolved, such as 15-60% dissolved, e.g. 45% dissolved, such as 20-40% dissolved, e.g. 30% dissolved.

The addition of guest molecules to the cyclodextrin can either be added admixed in the adsorption solution or as a separate step after the multi-layer has been formed on the solid material surface.

In yet another embodiment of the present invention, at least 5% of the cyclodextrin derivatives are complexed with at least one guest molecule, such as in the range of 5-100%, e.g. 10%, such as in the range of 15-95%, e.g. 20%, such as in the range of 30-85%, e.g. 40%, such as in the range of 50-75%, e.g. 60% of the cyclodextrin derivatives are complexed with at least one guest molecule.

In one embodiment, the amount of guest molecule in the adsorption solution is in the range from about 0.1% w/w to about 15% w/w, such as from about 0.1% w/w to about 10% w/w, such as from about 0.1% w/w to about 5% w/w, from about 0.5% w/w to about 10% w/w, such as from about 1% w/w to about 5% w/w.

The inventors of the present invention have found that in order to control the thickness of the multilayer, the type of carbon chain of the modified self assembling cyclodextrin, the concentration of the modified self assembling cyclodextrin in the adsorption solution, and the solvent composition of the adsorption solution may be adjusted.

One aspect of the present invention relates to a functionalized solid material, characterized in that the surface of the solid material contains at least 0.01 g/m$^2$ of one or more modified self assembling cyclodextrins, wherein at least one of the hydroxyl groups (—OH) of said cyclodextrin is modified to —O—(CO)$_n$R, wherein R is a straight or branched aliphatic chain of 1-50 carbons, such as 2-20 carbons, preferably 4-12 carbons, such as 4-8 carbons, and n is an integer from 0 to 1. Optionally, the chains may comprise halogens, alcohols, ethers, amines, carboxylic acids or other functional groups.

Still another aspect of the present invention relates to a functionalized solid material, characterized in that the surface of the solid material contains at least 0.003 g/m$^2$ of one or more modified self assembling or self aggregating cyclodextrins,
wherein at least one of the hydroxyl groups (—OH) of said cyclodextrin is modified to —O—(CO)$_n$R$^1$, —NR$^1$R$^2$, —SR$^1$, —N—COR$^1$, or —O—(CO)$_n$OR$^1$;
wherein R$^1$, R$^2$ are independently of one another being selected from hydrogen, alkyl, alkenyl, alkynyl, aryl, and heteroaryl;
R$^1$ and R$^2$, optionally linked with a bridge member Y$_n$, thereby forming one or more rings. Y$_n$ being a bond or a C1-12 alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, S(O)$_{1-2}$ or carbonyl, and wherein n is an integer between 1 and 12.

Still another aspect of the invention relates to a functionalized solid material, characterized in that the surface of the solid material contains at least 0.003 g/m$^2$ of one or more modified cyclodextrins, wherein at least one of the hydroxyl groups (—OH) of said cyclodextrin is modified to —O—(CO)$_n$R, wherein R is a straight or branched aliphatic chain of 1-50 carbons, such as 2-20 carbons, preferably 4-12 carbons, such as 4-8 carbons, and n is an integer from 0 to 1.

In one embodiment of the present invention, the at least one modified hydroxyl group is a primary hydroxyl group.

In another embodiment of the present invention, the at least one modified hydroxyl group is a secondary hydroxyl group.

In yet another embodiment of the present invention, the modified self assembling cyclodextrin is amphiphilic.

In the present context the term "amphiphilic" relates to a cyclodextrin possessing both hydrophilic and lipophilic properties.

In one embodiment, the surface of the solid material contains at least 0.02 g/m$^2$ of one or more modified self assembling cyclodextrins, such as at least 0.03 g/m$^2$, e.g. at least 0.04 g/m$^2$, 0.05, 0.06, 0.07, 0.08, 0.09, or 0.1 g/m$^2$.

In a further embodiment, the surface of the solid material contains at least 0.01 to 0.5 g/m$^2$ of one or more modified self assembling cyclodextrins, such as 0.02 to 0.4 g/m$^2$, e.g. 0.03 to 0.3 g/m$^2$, such as 0.04 to 0.2 g/m$^2$, e.g. 0.05 to 0.1 g/m$^2$.

In yet another embodiment, the surface of the solid material contains at least 0.003 to 0.1 g/m$^2$ of one or more modified self assembling or self aggregating cyclodextrins, such as 0.004 to 0.09 g/m$^2$, e.g. 0.005 to 0.08 g/m$^2$, such as 0.006 to 0.07 g/m$^2$, e.g. 0.007 to 0.06 g/m$^2$, such as 0.008 to 0.06 g/m$^2$, e.g. 0.009 to 0.05 g/m$^2$, such as 0.01 to 0.04 g/m$^2$, e.g. 0.02 to 0.03 g/m$^2$.

In yet another embodiment, the solid material is an absorbent item worn by a woman while she is menstruating, recovering from vaginal surgery, for lochia (post birth bleeding), abortion, or any other situation where it is necessary to absorb a flow of blood from a woman's vagina. Such an absorbant could be a sanitary napkin, sanitary towel, sanitary pad, menstrual pad, maxi pad, or pad.

In yet another embodiment, the solid material is an absorbent item worn by men or women who have urinary incontinence problems or experience stress incontinence. An incontinence pad is a similar item to a menstrual pad, perhaps with a high absorbency. Menstrual pads may be used by some people for this purpose.

In another embodiment, the solid material is a bandage. In the present context, the term "bandage" refers to a piece of material used either to support a medical device such as a dressing or splint, or on its own to provide support to the body. Bandages are available in a wide range of types, from generic cloth strips, to specialised shaped bandages designed for a specific limb or part of the body, although bandages can often be improvised as the situation demands, using clothing, blankets or other material.

In yet another embodiment, the solid material is a dressing. In the present context, the term "dressing" refers to an adjunct used by a person for application to a wound to promote healing and/or prevent further harm. A dressing is designed to be in direct contact with the wound, which makes it different from a bandage, which is primarily used to hold a dressing in place.

In still another embodiment, the solid material is a food or beverage storage container, e.g. a flask, canister, bottle, tray etc. Preferably the solid material is a bottle cap, e.g. the inner lining of the cap being in direct contact with the food or beverage.

In yet another embodiment, the solid material is a filter, e.g. as part of a filter or gas mask, as part of a gas, liquid or water purifying filter.

One type of guest molecules can be perfume. In the textile industry, perfume is used to deposit some fragrance on the textile, both to provide an olfactory aesthetic benefit and to serve as a signal that the fabrics are clean. Due to the high energy input and large air flow in the drying process used in the typical automatic laundry dryers, a large part of the perfume provided by such laundry products has been lost out the dryer vent. Even for the less volatile components, as described hereinafter, only a small fraction remains on the fabrics after the drying cycle. Thus, the present invention alleviates this problem by the production of textiles with a multi-layer cyclodextrin coating that retain the perfume by complexation. Without such a multi-layer cyclodextrin coating, the loss of the highly volatile fraction of the perfume, as described hereinafter, is very high. Usually, the loss of the highly volatile fraction is practically total. Due to this effect, most laundry perfumes have been composed mainly of less volatile, high boiling perfume components (having high boiling points) to survive the drying cycle. The main function of a small fraction of the highly volatile, low boiling perfume components (having low boiling points) in these perfumes is to improve the fragrance odor of the textile product itself, rather than impacting on the subsequent fabric odor. However, some of the volatile, low boiling perfume ingredients can provide a fresh and clean impression to the fabrics, and it is highly desirable that these ingredients be deposited and present on the dried textile fabrics.

The perfume ingredients and compositions of this invention are the conventional ones known in the art. Selection of any perfume component, or amount of perfume, is based solely on aesthetic considerations. Normally, the art recognized perfume compositions are relatively substantive as described hereinafter to maximize their odor effect on fabrics. However, it is a special advantage of perfume delivery via the perfume in softeners during the drying or washing process that non-substantive perfumes are effective, due to complexation with the multi-layer cyclodextrin coating on the textile surface. Hence, the present invention can lower the necessary content of substantive perfume in the softeners.

A substantive perfume is one that contains a sufficient percentage of substantive perfume materials so that when the perfume is used at normal levels in laundry products, it deposits a desired odor on the laundered textile fabrics. In general, the degree of substantivity of a perfume is roughly proportional to the percentages of substantive perfume material used.

Substantive perfume materials are those odorous compounds that deposit on fabrics via the laundry process and are detectable by people with normal olfactory acuity. Such materials typically have vapor pressures lower than that of the average perfume material. Also, they typically have molecular weights of about 200 or above, and are detectable at levels below those of the average perfume material.

Perfumes can also be classified according to their volatility, as mentioned hereinbefore. The highly volatile, low boiling, perfume ingredients typically have boiling points of about 250 degrees Celsius or lower. Many of the more moderately volatile perfume ingredients are also lost substantially in the drying cycle. The moderately volatile perfume ingredients are those having boiling points of from about 250 degrees Celsius to about degrees Celsius. The less volatile, high boiling, perfume ingredients referred to hereinbefore are those having boiling points of about 300 degrees Celsius or higher. A significant portion of even these high boiling perfume ingredients, considered to be fabric substantive, is lost during the drying cycle, and it is desirable to have means to retain more of these ingredients on the dried fabrics. Many of the perfume ingredients, along with their odor character, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo.menthyl acetate, menthone, iso-menthone, myrcene, myrcenyl acetate, myrcenol, nerol, neryl acetate, nonyl acetate, phenyl ethyl alcohol, alphapinene, beta-pinene, gamma-terpinene, alpha-terpineol, beta-ter-pineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95 DEG % of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gammamethyl ionone, nerolidol, patchouli alcohol, phenyl hexanol, betaselinene, trichloromethyl phenyl carbinyl acetate, triethyl citrate, vanillin, and veratraldehyde. Cedarwood terpenes are composed mainly of alpha-cedrene, beta-cedrene, and other C15 H24 sesquiterpenes.

Examples of the less volatile, high boiling, perfume ingredients are: benzophenone, benzyl salicylate, ethylene brassylate, galaxolide (1,3,4,6,7,8-hexahydro-4,6,6,7,8,8-hexamethyl-cyclopenta-gama-2-benzopyran), hexyl cinnamic aldehyde, lyral (4-(4-hydroxy-4-methyl pentyl)-3-cyclohexene-1O-carboxaldehyde), methyl cedrylone, methyl dihydro jasmonate, methyl-beta-naphthyl ketone, musk indanone, musk ketone, musk tibetene, and phenylethyl phenyl acetate.

Other types of guest molecules can be miticides, insecticides, fungicides, herbicides, rodenticides, insect repellents, tick repellents, animal repellents or mixtures thereof.

In one embodiment of the present invention, the guest molecule is an active pharmaceutical ingredient. The term "active pharmaceutical ingredient (API)" refers to the biologically active substance in a pharmaceutical drug, such as e.g. an anticancer drug, or an antibiotic.

Preferably, the multi-layer cyclodextrin coating on the solid material surface is stable to conditions during washing of a solid material such as washing temperature.

In one embodiment of the present invention, substantially all the multi-layer cyclodextrin coating stays on the solid material surface when said solid material surface is washed in water at 100 degrees Celsius or lower, such as in the range of 0-99 degrees Celsius, e.g. 80 degrees Celsius, such as in the range of 10-70 degrees Celsius, e.g. 65 degrees Celsius, such as in the range of 20-60 degrees Celsius, e.g. 55 degrees Celsius, such as in the range of 25-50 degrees Celsius, e.g. 45 degrees Celsius, such as in the range of 30-40 degrees Celsius, e.g. 35 degrees Celsius.

The term "substantially all" relates to at least 20% of the multi-layer cyclodextrin coating stays on the solid material surface during washing for 24 hours, such as in the range of 25-100%, e.g. 99%, such as in the range of 30-95%, e.g. 90%, such as in the range of 40-85%, e.g. 80%, such as in the range of 50-75%, e.g. 70%, such as in the range of 55-65%, e.g. 60% of the multi-layer cyclodextrin coating stays on the solid material surface during washing for 24 hours.

In one embodiment of the present invention, at least 1% of the self assembling cyclodextrin derivatives are complexed with at least one guest molecule, such as in the range of 5-100%, e.g. 99%, such as in the range of 15-95%, e.g. 90%, such as in the range of 25-85%, e.g. 80%, such as in the range of 35-75%, e.g. 70%, such as in the range of 45-65%, e.g. 60%, such as in the range of 55-60%, e.g. 50% of the self assembling cyclodextrin derivatives are complexed with at least one guest molecule.

In another embodiment of the present invention, the guest molecule is a perfume.

In yet another embodiment of the present invention, the guest molecule is a perfume comprising a mixture of one or more "high boiling" perfume ingredients and one or more "low boiling" perfume ingredients.

Another aspect of the present invention relates to an adsorption solution comprising at least one modified self assembling cyclodextrin and at least two solvents, characterized in that at least one of the hydroxyl groups (—OH) of the cyclodextrin is modified to —O—$(CO)_n$R, wherein R is a straight or branched aliphatic chain of 1-50 carbons, and n is an integer from 0 to 1, wherein at least one solvent is polar.

Another aspect of the present invention relates to an adsorption solution comprising at least one modified self assembling or self aggregating cyclodextrin and at least two solvents, characterized in that at least one of the hydroxyl groups (—OH) of the cyclodextrin is modified to —O—$(CO)_n$R$^1$, wherein R$^1$ is selected from hydrogen, alkyl, alkenyl, alkynyl, aryl, and heteroaryl.

Yet another aspect of the present invention relates to an adsorption solution comprising at least one modified self assembling or self aggregating cyclodextrin and at least one solvent, characterized in that at least one of the hydroxyl groups (—OH) of the cyclodextrin is modified to —O—$(CO)_n$R$^1$, wherein R$^1$ is selected from hydrogen, alkyl, alkenyl, alkynyl, aryl, and heteroaryl.

Still another aspect of the present invention relates to an adsorption solution comprising at least one modified self assembling or self aggregating cyclodextrin and at least one solvent, characterized in that at least one of the hydroxyl groups (—OH) of the cyclodextrin is modified to —O—$(CO)_n$R$^1$, wherein R$^1$ is a straight or branched aliphatic chain of 1-50 carbons, and n is an integer from 0 to 1.

Yet another aspect of the present invention relates to an adsorption solution comprising at least one modified self assembling cyclodextrin and at least two solvents, characterized in that at least one of the hydroxyl groups (—OH) of the cyclodextrin is modified to —O—$(NH)_n$R, wherein R is a straight or branched aliphatic chain of 1-50 carbons, such as 2-20 carbons, preferably 4-12 carbons, such as 4-8 carbons, and n is an integer from 0 to 1, wherein at least one solvent is polar.

Yet another aspect of the present invention relates to an adsorption solution comprising at least one modified self assembling or self aggregating cyclodextrin and at least one solvent, characterized in that at least one of the hydroxyl groups (—OH) of the cyclodextrin is modified to —NR$^1$R$^2$, wherein R$^1$ and R$^2$, independently of one another, is a straight or branched aliphatic chain of 1-50 carbons, such as 2-20 carbons, preferably 4-12 carbons, such as 4-8 carbons.

Still another aspect of the present invention relates to an adsorption solution comprising at least one modified self assembling or self aggregating cyclodextrin and at least one solvent, characterized in that at least one of the hydroxyl groups (—OH) of the cyclodextrin is modified to —NR$^1$R$^2$, wherein R$^1$, R$^2$ are independently of one another being selected from hydrogen, alkyl, alkenyl, alkynyl, aryl, and heteroaryl;

R$^1$ and R$^2$, optionally linked with a bridge member Y$_n$, thereby forming one or more rings. Y$_n$ being a bond or a C1-12 alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, $S(O)_{1-2}$ or carbonyl, and wherein n is an integer between 1 and 12.

Yet another aspect of the present invention relates to an adsorption solution comprising at least one modified self assembling or self aggregating cyclodextrin and at least one solvent, characterized in that at least one of the hydroxyl groups (—OH) of the cyclodextrin is modified to —SR$^1$, wherein R$^1$ is a straight or branched aliphatic chain of 1-50 carbons, such as 2-20 carbons, preferably 4-12 carbons, such as 4-8 carbons.

Still another aspect of the present invention relates to an adsorption solution comprising at least one modified self assembling or self aggregating cyclodextrin and at least one solvent, characterized in that at least one of the hydroxyl groups (—OH) of the cyclodextrin is modified to —SR$^1$, wherein R$^1$ is selected from hydrogen, alkyl, alkenyl, alkynyl, aryl, and heteroaryl.

Yet another aspect of the present invention relates to an adsorption solution comprising at least one modified self assembling or self aggregating cyclodextrin and at least one solvent, characterized in that at least one of the hydroxyl groups (—OH) of the cyclodextrin is modified to —N—COR$^1$, wherein R$^1$ is selected from hydrogen, alkyl, alkenyl, alkynyl, aryl, and heteroaryl.

Another aspect of the present invention relates to an adsorption solution comprising at least one modified self assembling or self aggregating cyclodextrin and at least one solvent, characterized in that at least one of the hydroxyl groups (—OH) of the cyclodextrin is modified to —N—COR$^1$, wherein R$^1$ is a straight or branched aliphatic chain of 1-50 carbons, such as 2-20 carbons, preferably 4-12 carbons, such as 4-8 carbons.

Yet another aspect of the present invention relates to an adsorption solution comprising at least one modified self assembling or self aggregating cyclodextrin and at least one solvent, characterized in that at least one of the hydroxyl groups (—OH) of the cyclodextrin is modified to —O—$(CO)_n$OR$^1$, wherein R$^1$ is selected from hydrogen, alkyl, alkenyl, alkynyl, aryl, and heteroaryl.

Still another aspect of the present invention relates to an adsorption solution comprising at least one modified self assembling or self aggregating cyclodextrin and at least one solvent, characterized in that at least one of the hydroxyl groups (—OH) of the cyclodextrin is modified to —O—$(CO)_n$OR$^1$, wherein R$^1$ is a straight or branched aliphatic chain of 1-50 carbons, such as 2-20 carbons, preferably 4-12 carbons, such as 4-8 carbons.

In one embodiment of the present invention, the adsorption solution comprises at least one solvent.

In another embodiment of the present invention, the adsorption solution comprises at least one solvent, wherein at least one solvent is polar.

In another embodiment of the present invention, the adsorption solution comprises at least one solvent, wherein at least one solvent is apolar.

In still another embodiment of the present invention, the adsorption solution comprises at least two solvents.

In another embodiment of the present invention, the adsorption solution comprises at least two solvents, wherein at least one solvent is polar.

In yet another embodiment of the present invention, at least one solvent is polar.

Form a ring means that the atoms mentioned are connected through a bond such that the ring structure is formed. The term "ring" is used synonymously with the term "cyclic".

Alkyl group: the term "alkyl" means a saturated linear, branched or cyclic hydrocarbon group including, for example, methyl, ethyl, isopropyl, t-butyl, heptyl, dodecyl, octadecyl, amyl, 2-ethylhexyl, and the like. Preferred alkyls are lower alkyls, i.e. alkyls having 1 to 10 carbon atoms, such as 1, 2, 3, 4, 5, 6, 7 or 8 carbon atoms. A cyclic alkyl/cycloalkyl means a saturated carbocyclic compound consisting of one or two rings, of three to eight carbons per ring, which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, aryl-aminosulfonyl, alkylsulfonylamino, arylsulfonylamino, alkylaminocarbonyl, arylamino-carbonyl, alkylcarbonylamino and arylcarbonylamino. The alkyl group may also be understood as a heteroalkyl. A heteroalkyl is a saturated linear, branched or cyclic hydrocarbon group (including, for example, methyl, ethyl, isopropyl, t-butyl, heptyl, dodecyl, octadecyl, amyl, 2-ethylhexyl, and the like) wherein one or more carbon atoms are substituted for a heteroatom selected from N, O, S, $S(O)_{1-2}$, Si or P and which can optionally be substituted with one or more substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, aryl-aminocarbonyl, alkylcarbonylamino, or arylcarbonylamino. Heteroalkyls of the present invention may be branched or unbranched or forming a ring and may range from one (1) to fifty (50) carbon atoms in length wherein 50% or less, of said carbon atoms may be substituted for N, NH(Q-4), O, S, $S(O)_{1-2}$, Si, P, Cl, Br. A cyclic heteroalkyl/heterocyclyl means a saturated cyclic compound or part of a compound, consisting of one to more rings, of three to eight atoms per ring, incorporating one, two, three or four ring heteroatoms, selected from N, O or $S(O)_{1-2}$, and which can optionally be substituted with one or two substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, arylaminocarbonyl, alkylcarbonylamino, or arylcarbonylamino. Examples of common heterocyclyls of the present invention include, but are not limited to piperazine and piperidine which may thus be heterocyclyl substituents as defined herein. Such substituents may also be denoted piperazino and piperidino respectively. A further heterocyclyl of the present invention is thiophene.

If the radical (R) is an alkyl group, in which, in addition, one $CH_2$ group (alkoxy or oxaalkyl) may be replaced by an O atom, it may be straight-chain or branched. It preferably has 2, 3, 4, 5, 6, 7, 8, 9 or 12 carbon atoms and accordingly is preferably ethyl, propyl, butyl, pentyl, hexyl, heptyl, octyl, nonyl, decyl, ethoxy, propoxy, butoxy, pentoxy, hexyloxy, heptyloxy, octyloxy, nonyloxy or decyloxy, furthermore also undecyl, dodecyl, undecyloxy, dodecyloxy, 2-oxapropyl (=2-methoxymethyl), 2-oxabutyl (=methoxyethyl) or 3-oxabutyl (=2-ethoxymethyl), 2-, 3- or 4-oxapentyl, 2-, 3-, 4- or 5-oxahexyl, or 2-, 3-, 4-, 5- or 6-oxaheptyl.

Particular preference is given to hexyl, pentyl, butyl, n-butyl, propyl, i-propyl, methyl and ethyl, in particular propyl and pentyl; particularly preferred alkoxy groups are hexyloxy, pentoxy, n-butoxy, propoxy, i-propoxy, methoxy and ethoxy, in particular ethoxy and n-butoxy.

Preferred branched radicals are isopropyl, 2-butyl (=1-methylpropyl), isobutyl (=3-methylpropyl), tert-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexyloxy, 1-methylhexyloxy, 1-methylheptyloxy, 2-oxa-3-methylbutyl and 3-oxa-4-methylpentyl.

The radical R may also be an optically active organic radical containing one or more asymmetrical carbon atoms.

Halogen preferably represents chlorine, but may also be bromine, fluorine or iodine.

Alkenyl group: the term "alkenyl" means a non-saturated linear, branched or cyclic hydrocarbon group including, for example, methylene or ethylene. Preferred alkenyls are lower alkenyls, i.e. alkenyls having 1 to 10 carbon atoms, such as 1, 2, 3, 4, 5 or 8 carbon atoms. A cyclic alkenyl/cycloalkenyl means a non-saturated carbocyclic compound consisting of one or two rings, of three to eight carbons per ring, which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, aryl-aminosulfonyl, alkylsulfonylamino, arylsulfonylamino, alkylaminocarbonyl, arylamino-carbonyl, alkylcarbonylamino and arylcarbonylamino. The alkenyl group may also be understood as a heteroalkenyl. A heteroalkenyl is a non-saturated linear, branched or cyclic hydrocarbon group (including, for example, methyl, ethyl, isopropyl, t-butyl, heptyl, dodecyl, octadecyl, amyl, 2-ethylhexyl, and the like) wherein one or more carbon atoms are substituted for a heteroatom selected from N, O, S, $S(O)_{1-2}$, Si or P and which can optionally be substituted with one or more substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, aryl-aminocarbonyl, alkylcarbonylamino, or arylcarbonylamino. Heteroalkenyls of the present invention may be branched or unbranched or forming a ring and may range from one (1) to fifty (50) carbon atoms in length wherein 50% or less, of said carbon atoms may be substituted for N, NH(Q-4), O, S, $S(O)_{1-2}$, Si, P, Cl, Br. A cyclic heteroalkenyl means a non-saturated cyclic compound or part of a compound, consisting of one or more rings, of three to eight atoms per ring, incorporating one, two, three or four ring heteroatoms, selected from N, O or $S(O)_{1-2}$, and which can optionally be substituted with one or two substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, arylaminocarbonyl, alkylcarbonylamino, or arylcarbonylamino.

Alkynyl group: the term "alkynyl" means a non-saturated linear or branched hydrocarbon group including, for example, ethynyl or propynyl. Preferred alkynyls are lower alkynyls, i.e. alkynyls having 1 to 10 carbon atoms, such as 1, 2, 3, 4, 5 or 9 carbon atoms.

The acyl radical has the formula RCO, where R represents an alkyl group that is attached to the CO group with a single bond. Examples of acyl radicals are alkanoyl, aroyl, lower alkoxycarbonyl, or N,N-di-lower alkylcarbamoyl, preferably lower alkanoyl.

Acyl in acyloxy represents lower alkanoyl, aroyl, lower alkoxycarbonyl, or N,N-di-lower alkylcarbamoyl, preferably lower alkanoyl.

Lower alkanoyl is preferably acetyl, propionyl, butyryl, or pivaloyl, especially acetyl.

Aroyl is preferably benzoyl; and also e.g. benzoyl substituted by one or two of lower alkyl, lower alkoxy, halogen or trifluoromethyl; aroyl is also e.g. thienoyl, pyrroloyl, 2-, 3- or 4-pyridylcarbonyl, advantageously nicotinoyl.

Lower alkanoyloxy is preferably acetoxy; and also e.g. pivaloyloxy or propionyloxy.

Aroyloxy is preferably benzoyloxy; and also e.g. benzoyloxy substituted on the benzene ring by one or two of lower alkyl, lower alkoxy, halogen or trifluoromethyl.

Heteroaroyloxy is preferably 2-, 3- or 4-pyridylcarbonyloxy, advantageously nicotinoyloxy.

Aryl represents a hydrocarbon comprising at least one aromatic ring, and may contain from 5 to 18, preferably from 6 to 14, more preferably from 6 to 10, and most preferably 6 carbon atoms. Typical aryl groups include phenyl, naphthyl, phenanthryl, anthracyl, indenyl, azulenyl, biphenylenyl, and fluorenyl groups. Particularly preferred aryl groups include phenyl, naphthyl and fluorenyl, with phenyl being most preferable. Hence, aryl represents a carbocyclic or heterocyclic aromatic radical comprising e.g. optionally substituted phenyl, naphthyl, pyridyl, thienyl, indolyl or furyl, preferably phenyl, naphthyl, pyridyl, thienyl, indolyl or furyl, and especially phenyl. Non-limiting examples of substituents are halogen, alkyl, alkenyl, alkoxy, cyano and aryl.

A carbocyclic aromatic radical represents preferably phenyl or phenyl substituted by one or two substituents selected from lower alkyl, lower alkoxy, hydroxy, acyloxy, nitro, amino, halogen, trifluoromethyl, cyano, carboxy, carboxy functionalized in form of a pharmaceutically acceptable ester or amide, lower alkanoyl, aroyl, lower alkylsulfonyl, sulfamoyl, N-lower alkylsulfamoyl and N,N-di-lower alkylsulfamoyl; also 1- or 2-naphthyl, optionally substituted by lower alkyl, lower alkoxy, cyano or halogen.

A heterocyclic aromatic radical represents particularly thienyl, indolyl, pyridyl, furyl; and also e.g. a said heterocyclic radical monosubstituted by lower alkyl, lower alkoxy, cyano or halogen.

Thienyl represents 2- or 3-thienyl, preferably 2-thienyl.

Pyridyl represents 2-, 3- or 4-pyridyl, preferably 3- or 4-pyridyl advantageously 3-pyridyl.

Furyl represents 2- or 3-furyl, preferably 3-furyl.

Indolyl represents preferably 3-indolyl.

Heteroaryl means an aromatic cyclic compound or part of a compound having one or more rings, of four to eight atoms per ring, incorporating one, two, three or four heteroatoms (selected from nitrogen, oxygen, or sulfur) within the ring which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonlamino and arylcarbonylamino.

Substituted lower alkyl means a lower alkyl having one to three substituents selected from the group consisting of hydroxyl, alkoxy, amino, amido, carboxyl, acyl, halogen, cyano, nitro and thiol.

The term "lower" referred to above and hereinafter in connection with organic radicals or compounds respectively preferably defines such with up to and including 10, preferably up to and including 7 and advantageously one or two carbon atoms.

A lower alkyl group preferably contains 1-4 carbon atoms and represents for example ethyl, propyl, butyl or advantageously methyl.

A lower alkenyl group preferably contains 2-4 carbon atoms and represents for example allyl or crotyl.

A lower alkoxy group preferably contains 1-4 carbon atoms and represents for example methoxy, propoxy, isopropoxy or advantageously ethoxy.

To completely avoid a specific drying process, or simply to reduce the processing time and energy consumption, it could be an advantage to use solvents with a low boiling point in the adsorption solution.

In one embodiment of the present invention, the boiling point of the solvents is below 150 degrees Celsius, such as in the range of 20-140 degrees Celsius, e.g. 130 degrees Celsius, such as in the range of 30-120 degrees Celsius, e.g. 110 degrees Celsius, such as in the range of 40-100 degrees Celsius, e.g. 95 degrees Celsius, such as in the range of 45-90 degrees Celsius, e.g. 80 degrees Celsius, such as in the range of 50-75 degrees Celsius, e.g. 65 degrees Celsius.

In a preferred embodiment of the present invention, the solvents for the adsorption solution are selected from the group consisting of water, ethanol, methanol, butanol, isopropanol, tetrahydrofuran and acetone. In a further preferred embodiment, the adsorption solution comprises water and ethanol.

In another embodiment of the present invention, the solvents for the adsorption solution are selected from the group consisting of water, ethanol, methanol, butanol, isopropanol, tetrahydrofuran, chloroform, propanol, methyl acetate and acetone.

In one embodiment of the present invention, the adsorption solution comprises at least one modified self assembling cyclodextrin, wherein at least one modified hydroxyl group of the cyclodextrin is a primary hydroxyl group.

In another embodiment of the present invention, the adsorption solution comprises at least one modified self assembling cyclodextrin, wherein at least one modified hydroxyl group of the cyclodextrin is a secondary hydroxyl group.

In yet another embodiment of the present invention, the adsorption solution comprises at least one modified self assembling cyclodextrin being amphiphilic.

In still another embodiment of the present invention, the adsorption solution further comprises one or more types of guest molecules (for complexing with the cyclodextrin).

In still another embodiment of the present invention, the sanitary napkin, sanitary towel, sanitary pad, menstrual pad, maxi pad, or pad is an absorbent item worn by a woman while she is menstruating, recovering from vaginal surgery, for lochia (post birth bleeding), abortion, or any other situation where it is necessary to absorb a flow of blood from a woman's vagina.

These pads are not to be confused with incontinence pads, which are worn by men or women who have urinary incontinence problems or experience stress incontinence. An incontinence pad is a similar item to a menstrual pad, perhaps with a high absorbency. Menstrual pads may be used by some people for this purpose.

In yet another embodiment of the present invention, the guest molecule is iodine, e.g. radioactive iodine (i.e. iodine-131).

In another embodiment of the present invention, the guest molecule is a perfume.

In yet another embodiment of the present invention, the guest molecule is a perfume comprising a mixture of one or more "high boiling" perfume ingredients and one or more "low boiling" perfume ingredients.

In another embodiment of the present invention, the adsorption solution has a turbidity of 500 Nephelometric Turbidity Units (NTU) or less, such as in the range of 0-450, e.g. 400, such as in the range of 5-350, e.g. 300, such as in the range of 10-250, e.g. 200, such as in the range of 15-150, e.g. 140, such as in the range of 20-130, e.g. 125, such as in the range of 25-110, e.g. 100, such as in the range of 30-90, e.g. 80, such as in the range of 35-75, e.g. 70, such as in the range of 40-65, e.g. 50 Nephelometric Turbidity Units (NTU).

In another embodiment of the present invention, the adsorption solution has a turbidity of 500 Nephelometric Turbidity Units (NTU) or higher, such as in the range of 550-70000, e.g. 1000, such as in the range of 1500-60000, e.g. 2000, such as in the range of 2500-50000, e.g. 3000, such as in the range of 4000-40000, e.g. 5000, such as in the range of 6000-30000, e.g. 7000, such as in the range of 9000-20000, e.g. 10000, such as in the range of 11000-19000, e.g. 12000, such as in the range of 13000-18000, e.g. 14000, such as in the range of 15000-17000, e.g. 16000 Nephelometric Turbidity Units (NTU).

Still another aspect of the present invention is to provide a modified cyclodextrin, wherein
at least one of the hydroxyl groups (—OH) of the cyclodextrin is modified to —O—(CO)$_n$R,
R is a straight or branched aliphatic chain of 1-50 carbons, such as 2-20 carbons, preferably 4-12 carbons, such as 4-8 carbons, and n is an integer from 0 to 1, and said modified cyclodextrin is substantially free of the corresponding unmodified cyclodextrin.

Yet another aspect of the present invention relates to a modified cyclodextrin, wherein at least one of the hydroxyl groups (—OH) of said cyclodextrin is modified to —O—(CO)$_n$R$^1$, —NR$^1$R$^2$, —SR$^1$, —N—COR$^1$, or —O—(CO)$_n$OR$^1$;
wherein R$^1$, R$^2$ are independently of one another being selected from hydrogen, alkyl, alkenyl, alkynyl, aryl, and heteroaryl;

R$^1$ and R$^2$, optionally linked with a bridge member Y$_n$, thereby forming one or more rings. Y$_n$ being a bond or a C1-12 alkyl or an aryl, a carbocyclic, a heterocyclic or a heteroaromatic structure having 1-3 rings, 3-8 ring members in each and 0 to 4 heteroatoms, or a heteroalkyl comprising 1 to 12 heteroatoms selected from the group consisting of N, O, S, S(O)$_{1-2}$ or carbonyl, and wherein n is an integer between 1 and 12, and
said modified cyclodextrin is substantially free of the corresponding unmodified cyclodextrin.

The term "substantially free" relates to a modified cyclodextrin according to the invention comprising (or contaminated with) at most 0.1% of the corresponding unmodified cyclodextrin, such as at most 0.01%, e.g. at most 0.001%, such as at most 0.0001%, e.g. at most 0.00001%.

In the context of the present invention, when referring to "the corresponding unmodified cyclodextrin", it means that for modified α-, β-, and γ-CD "the corresponding unmodified cyclodextrin" is unmodified α-, β-, and γ-CD, respectively.

In a preferred embodiment, the present invention concerns a modified β-cyclodextrin wherein
at least one of the hydroxyl groups (—OH) of the β-cyclodextrin is modified to —O—(CO)$_n$R,
R is a straight or branched aliphatic chain of 1-50 carbons, such as 2-20 carbons, preferably 4-12 carbons, such as 4-8 carbons, and n is an integer from 0 to 1, and said modified β-cyclodextrin is substantially free of the corresponding unmodified β-cyclodextrin.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Materials

β-CD was purchased from Wacker Chemie AG (Munich, Germany). β-CD was dried at 110° C. under vacuum for 24 hours prior to use. Butyryl chloride, Hexanoyl chloride, Octanoyl chloride, phenol and sulfuric acid was purchased from Sigma Aldrich (Saint Louis, USA) and used as received. Pyridine was purchased from Sigma Aldrich and dried using molecular sieves prior to use (4 Å, Sigma Aldrich). Polypropylene (PP) nonwoven fibers were supplied by Fibertex A/S (DK) and consisted of only PP with no surface treatment such as lubricant as often found on PP nonwoven fibers. The fibers used had a weight of 10 g/m$^2$ (gram per square meter) with an average fiber diameter of 20 μm (micrometer) for the outer layer of fibers. Ethanol 96% v/v and 99.9% v/v was purchased from Kemetyl (Køge, DK) and used as received.

Synthesis

The β-CD was derivatized using a modified method of Gallois-Montbrun et al. ["Direct synthesis of novel amphiphilic cyclodextrin". Journal of Inclusion Phenomena and Macrocyclic Chemistry, 57:131-135, 2007]. 10 g of dried β-CD was added slowly to 150 ml pyridine under stirring. After partly dissolving the β-CD, 7 ml of alkyl chloride was added. After 30 minutes of reaction, 1 ml of water was added drop wise which turned the liquid from opaque to clear.

After 20 hours of reaction the pyridine with product was added drop wise to 4 liters of 2M HCl in order to precipitate the product. After precipitation the product was collected by filtration and redisolved in 100 ml 99.9% EtOH. The EtOH solution was added drop wise to 2l of saturated NaCl solution. The precipitate was collected and freeze dried overnight. The inventors of the present application have found that this precipitation process gives a low content of NaCl in the final product, but removes all native β-CD, butyryl chloride and pyridine from the final product. Modified CD synthesized from butyryl chloride, hexanoyl chloride and octanoyl chloride, all prepared according to this method, are denoted C4, C6 and C8, respectively.

General Application

The CD was dried under vacuum at 70° C. for 5 hours prior to use. CD and ethanol was mixed until a clear mixture was obtained, after which water was added to the mixture to obtain 10 ml of the desired concentration. A piece of polypropylene (PP) non-woven was cut with a weight of approximately 15 mg and added to the solution. The tube was transferred to a shaking table and shaked overnight at 120 Hz. After shaking, the PP non-woven was removed from the tube and washed with running water for 120 seconds to remove all solvent and non-bound CD. The coated PP non-woven was dried at room temperature for 5 hours and cut into 3 nearly identical pieces. Each piece was weighed and the weight noted before the pieces were measured by use of the phenol assay.

Phenol Assay

To determine the CD concentration on the sheets after the application, a modified phenol essay was used. For a standard curve a 100, 80, 60, 40, 30, 20, 15, 10, 8, 6, 4, 2 and 0 ppm was produced from native CD. A 1.2 or 2 ml sample of each concentration was added to a pyrex tube and 5 or 7 ml, respectively, of $H_2SO_4$ was added cautiously. The tubes were whirl mixed and transferred to a heating bath preset at 50±2° C. for 3 hours. After heating, the tubes were cooled to room temperature and 150 μL, 90 v/v %, phenol was added (9.4 g phenol mixed with 1.1 ml water). After addition of the phenol, the tubes were whirl mixed and then allowed to react for 1 hour at room temperature, after which they were whirl mixed again and measured by use of UV-vis at 487 nm. For analysis of the PP non-woven, a 4.5-6.0 mg sample of each sample was put into a pyrex tube and 1.2 or 2 ml of water was added. The PP non woven were pushed under the water to avoid side reactions between the pure $H_2SO_4$ and PP non-woven. After the non-woven sample was submerged under water, 5 or 7 ml $H_2SO_4$ were carefully added to the tube. After addition of $H_2SO_4$, the pyrex tubes containing the samples were treated identically to the tubes containing the standards.

To correlate the data obtained from the samples to the amount of CD coated onto the surface, pure CD was measured. Stock solutions were made from all types of CD comprising respectively 100, 60 and 20 ppm CD in 5% EtOH/$H_2O$, which were used to measure the CD content by use of the phenol assay.

A 15.3 mg of PP non-woven were shaken overnight in a solution of 10 ml 6.23 mg CD/ml 25% v/v (EtOH/water). After shaking, the PP non-woven was washed for 120 seconds under running tap water to remove leftover solution and unabsorbed CD. After washing, the sheet was dried at 40° C. for 2 hours. After drying, the sheet was transferred to a Soxhlet setup and Soxhlet extraction was run with water for 20 hours. After Soxhlet the sheet was dried at 40° C. for 5 hours and then washed with Ethanol.

Studies on (C4) modified self assembling β-CD concentration in the adsorption solution Experiments were done to determine the concentration in an adsorption solution (25 v/v % (EtOH/water)) of a modified self assembling β-CD that gives a measurable coating of the polypropylene (PP) non-woven under the parameters used. To compare the modified self assembling β-CD with native β-CD, both were tested in the concentration experiment as shown in the example in FIG. 1 (β-CD modified as ether with a straight carbon chain with four carbons (C4)). In the specific example, it was noted that the adsorption solutions turned turbid above a concentration of 6.23 mg β-CD/ml 25 v/v % (EtOH/water). It is expected that micelles or aggregates of modified self assembling β-CD is causing the turbidity.

Figure 1:
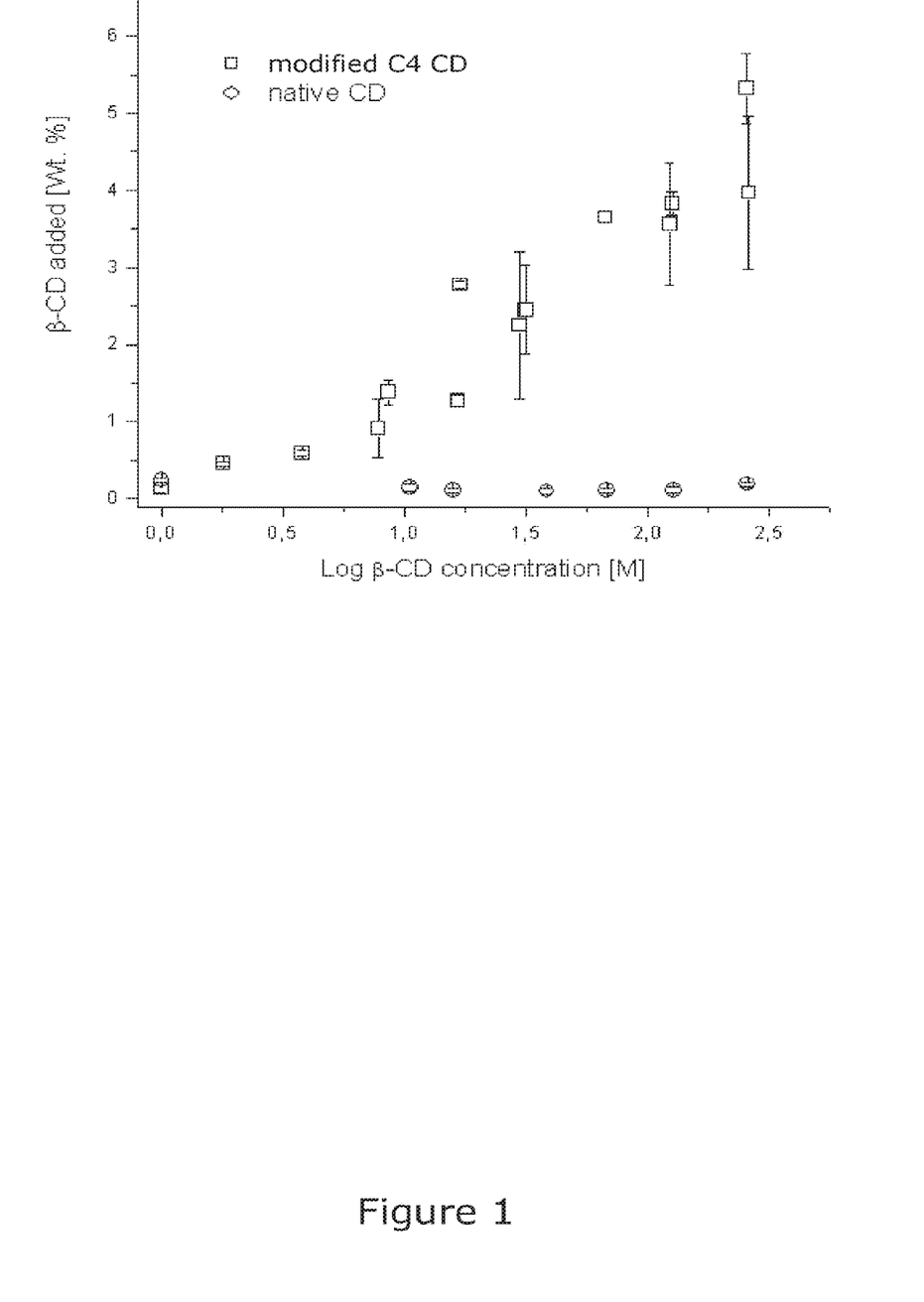
FIG. 1 shows the amount of (C4) modified self assembling β-CD adsorbed onto a PP non-woven fiber using different concentrations. The concentrations are scaled by log to better show the correlation between them. For comparison, the amount of non-modified β-CD adsorbed onto identical PP non-woven fibers is also shown.

The coating in weight percent is clearly much higher for the modified self assembling β-CD which at high concentrations have a 5 Wt. % coating, whereas the native β-CD reaches a maximum at 0.2 Wt. %. The amount of adsorbed modified self assembling β-CD increases with increased concentration, whereas the native CD keeps a relative constant level of approximately 0.2 Wt. %. The maximum coating was achieved when using a concentration of modified self assembling β-CD corresponding to 12.8 mg/ml which is relative close to the solubility limit of native β-CD. Using 0.045 mg/ml of modified self assembling β-CD gave a coating of 0.45 Wt. %, which is over double the maximum achieved with native β-CD, and which was achieved with at concentration of 6.43 mg/ml β-CD/ml 25 v/v % (EtOH/water). Thus, the modified self assembling β-CD has a much higher affinity for coating of PP non-woven compared to the native β-CD.

Studies on the Solvent Composition in the Adsorption Solution

Figure 2:
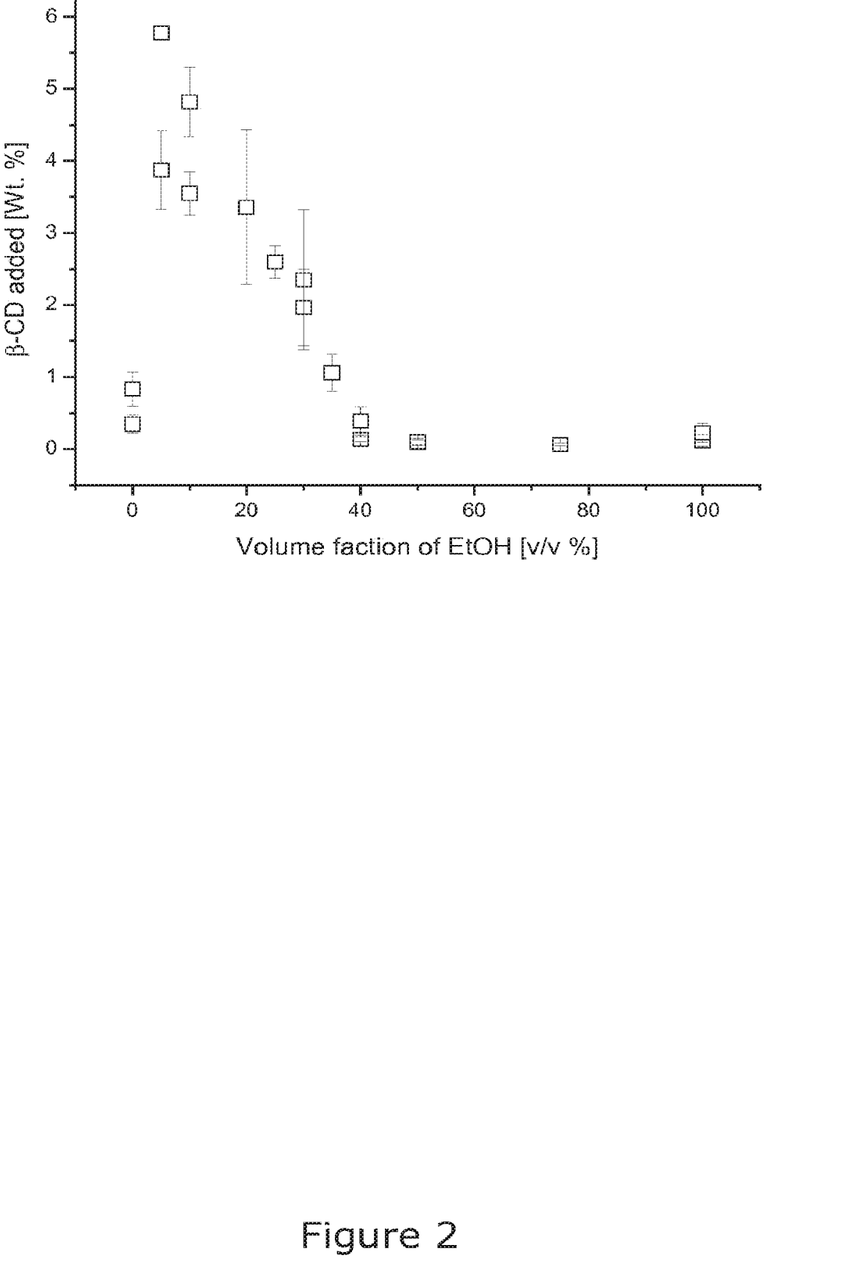
FIG. 2 shows the amount of adsorbed (C4) modified self assembling β-CD on a PP non-woven fiber as a function of varying EtOH/water ratios (vol/vol). For each point, a minimum of two pieces of PP non-woven was used and each PP piece measured at least twice.

As the (C4) modified self assembling β-CD formed a turbid solution at higher concentration, the effect of the solvent was investigated as the driving force for formation of aggregates or micelles. A solvent system of water and ethanol was investigated. A concentration of 0.85 mg/ml of (C4) modified self assembling β-CD was used for all experiments. The ratio between ethanol and water was changed resulting in different adsorptions to the PP non-woven as shown in FIG. 2.

It is evident from the solvent composition experiments that the solvent plays a vital role for adsorption. When no ethanol is used the (C4) modified self assembling β-CD is insoluble and the transport of CD from the adsorption solution onto the PP non-woven fiber is very low. Little coating is achieved when the adsorption solution is transparent, although the coating is 3-4 times higher than the coating achieved with native CD. When dissolving the (C4) modified self assembling β-CD in ethanol first and then adding water until a solvent composition from 5 to 35 v/v % (EtOH/water) is reached, the solution obtained is opaque. Additionally, within the before-mentioned concentration range, the largest coating percent is achieved. It is expected that the opaque solution is (C4) modified self assembling β-CD in the form of micelles or aggregates. These forms are expected to be thermodynamically unstable and, thus, being the driving force for adsorption of the (C4) modified self assembling β-CD onto the PP non-woven fiber. The more unstable the suspension, the larger the driving force for adsorption becomes.

Figure 3:
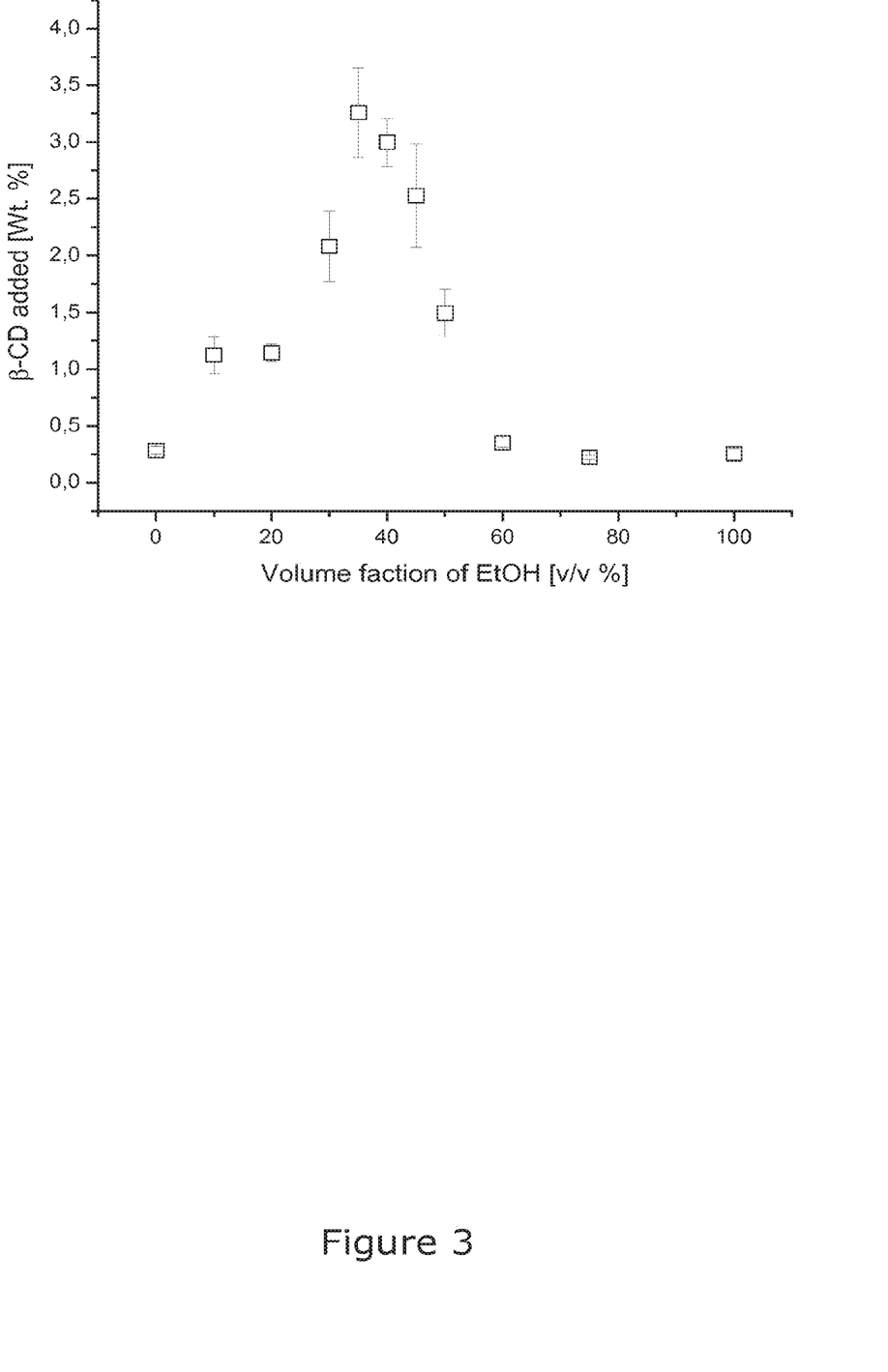
FIG. 3 shows the amount of adsorbed (C6) modified self assembling β-CD on a PP non-woven fiber as a function of varying EtOH/water ratios (vol/vol). For each point a minimum of two pieces of PP non-woven is used and each PP piece measured at least twice.
Figure 4:
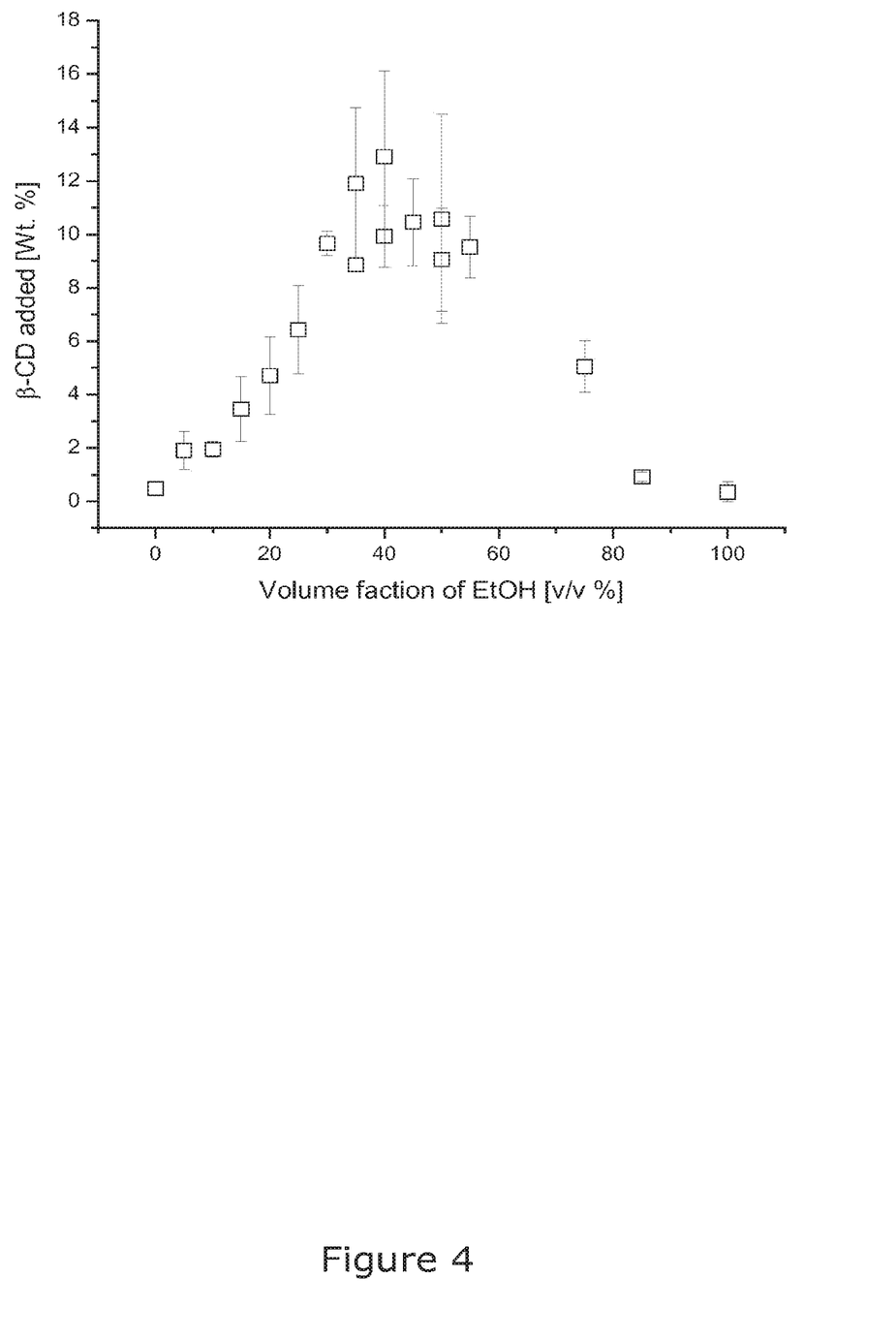
FIG. 4 shows the amount of adsorbed (C8) modified self assembling β-CD on a PP non-woven fiber as a function of varying EtOH/water ratios (vol/vol). For each point a minimum of two pieces of PP non-woven is used and each PP piece measured at least twice.

Thus, it is expected that the most unstable suspension is optimal for coating. When the fraction of EtOH becomes large enough to stabilize the solvated (C4) modified self assembling β-CD, the adsorption solution stays clear and little adsorption is measured on the PP non-woven fiber. If the formation of micelles or aggregates is the driving force for the adsorption of (C4) modified self assembling β-CD onto a PP non-woven fiber, then the length and number of arms on the modified CD will be an important parameter for the adsorption. The different solvent compositions were also tested for systems containing (C6) and (C8) modified self assembling β-CD, as shown in FIGS. 3 and 4.

The figures of (C4), (C6) and (C8) modified self assembling β-CD adsorption show that the maximum adsorption onto PP non-woven is clearly reached at different solvent (ethanol) concentrations. For (C8) self assembling β-CD, the coated amount of CD is up to 13.7 Wt. % which is a large coating degree. As the (C8) self assembling β-CD contains the most apolar groups, it is also expected that these have the highest affinity for coating an apolar surface such as PP non-woven fibers.

From TOF SIMS images (not shown), it is clear that an even distribution of the (C4), (C6) and (C8) modified self assembling β-CD is achieved by the coating procedure used.

Washing Resistance Experiments

Experiments with Soxhlet extraction (20 hours with refluxing water) of the coated PP non-woven fiber clearly show that the coated PP non-woven fiber is stable under such conditions. Generally, a solid material containing some of the desired compound is placed inside a thimble made from thick filter paper, which is loaded into the main chamber of the Soxhlet extractor. The Soxhlet extractor is placed onto a flask containing the extraction solvent. The Soxhlet is then equipped with a condenser. The solvent is heated to reflux. The solvent vapour travels up a distillation arm of the Soxhlet extractor and floods into the Soxhlet extractor chamber, housing the solid material. The condenser ensures that any solvent vapour cools, and drips back down into the chamber housing the solid material. The chamber containing the solid material slowly fills with warm solvent. Some of the compound may then dissolve in the warm solvent. When the Soxhlet chamber is almost full, the chamber is automatically emptied by a siphon side arm of the Soxhlet extractor, with the solvent running back down to the distillation flask. This cycle may be allowed to repeat many times, over hours or days.

During each cycle, a portion of the solid material may dissolve in the solvent. After many cycles the dissolved solid material is concentrated in the distillation flask. The advantage of this system is that instead of many portions of warm solvent being passed through the sample, just one batch of solvent is recycled. After extraction the solvent is removed, typically by means of a rotary evaporator, yielding the extracted solid material.

Coating

In this section, a number of the most significant experiments will be presented. The coatings are either prepared in the laboratory or at a larger scale at a pilot line. All experiments are verified the same way using the strike through method, which is a standardized method used in the industry.

Pilot Line Contra Lab Coating

As the textiles are treated differently in the lab compared to the machinery of the pilot line, the coating could be different. The coating technique in the lab is performed on small pieces of PPN (polypropylene) and with all parameters accounted for (weight, drying, coating degree, exposure type and time, solution). In the lab, the standard method is to use a tray with a ACD solution (adsorption solution comprising at least one modified self assembling cyclodextrin), dipping the PPN sheet for a certain amount of time followed by drying of the sheet. After drying, the PPN sheet is weighted again and the mass of coated ACD is easily determined. Several steps can be included like prolonged exposure, rinsing, partly redisolve and more.

At the pilot line, the method is the same always, with a few varying parameters. A model of the pilot line is sketched in FIG. 5.

Figure 5:
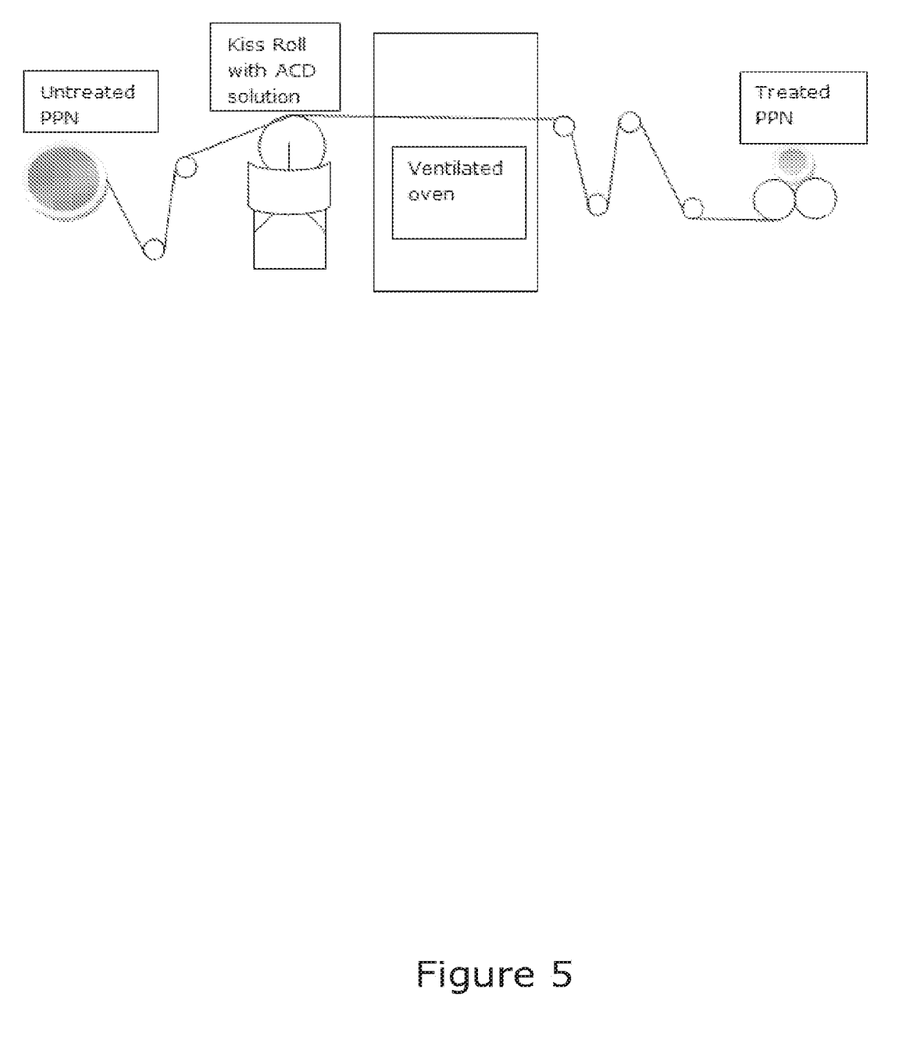
FIG. 5 shows a model of a pilot line for use in the present invention.

First, the untreated PPN is rolled across a Kiss-Roll system, which contains an ACD solution. Depending on the rotational velocity of the Kiss-Roll, how fast the PPN is moving, and how well the solution sticks to the Kiss-Roll, the PPN is wetted with the solution. The next step is a fast drying of the PPN in a ventilated oven, followed by a collecting roll. The adjustable variables are: Kiss Roll type and velocity, PPN velocity, oven temperature, even though a fully dried PPN is preferred, and of course the ACD solution and the type of PPN. Some variables affect each other; e.g. if the velocity of PPN is high, the oven temperature must be higher to ensure drying, or the ACD solution contains a lot of water compared to ethanol, the Kiss-Roll velocity must be higher to ensure wetting etc.

Strike Through Test

The Strike Through test (ST) is a method to compare how well an amount of water (in this case, a 0.9% NaCl solution in water, 5 ml.) is adsorbed through the textile. The system consists of a water chamber, which is opened with a button, also starting a timer. The water is transferred to a compartment which is in direct contact with the textile to be tested. Below the textile are several layers of highly absorbing paper, which are changed for every 5th measurement to ensure the absorption of the water. When the water has passed through the textile, the timer stops. The faster the water is transferred through the textile, the lower the strike through time, and thus the strike through time is a comparable factor when testing different textiles or treatment. In the coating experiments, the ST time is referred to as the strike through time, and that will be the major foundation for comparison.

The results are summarized in the below tables.

TABLE 2

Effect of ethanol/water content and ACD content on degree of coatning and strikethrough performance.

| Ethanol content % | ACD content[1] mg/ml | Degree of coatning % weight increase | Strikethrough score[2] |
|---|---|---|---|
| 10.0 | 0.0 | 0.4 | 5 |
| 10.0 | 1.0 | 2.5 | 2 |
| 10.0 | 1.0 | 1.8 | 2 |
| 10.0 | 5.0 | 10.8 | 3 |
| 10.0 | 5.0 | 4.8 | 2 |
| 20.0 | 0.0 | 0.0 | 5 |
| 20.0 | 1.0 | 0.3 | 1 |
| 20.0 | 1.0 | 2.3 | 4 |
| 20.0 | 5.0 | 1.1 | 3 |
| 20.0 | 5.0 | 8.0 | 3 |
| 50.0 | 0.0 | 6.8 | 5 |
| 50.0 | 1.0 | 0.0 | 2 |
| 50.0 | 1.0 | 0.5 | 1 |
| 50.0 | 5.0 | 1.3 | 1 |
| 50.0 | 5.0 | 1.1 | 1 |
| 96.0 | 0.0 | 5.8 | 5 |
| 96.0 | 1.0 | 3.5 | 3 |
| 96.0 | 1.0 | 0.0 | 1 |
| 96.0 | 5.0 | 0.6 | 1 |
| 96.0 | 5.0 | 1.3 | 1 |

[1]C4 modified β-CD, DS from 6-12.
[2]1—excellent performance, 5—very poor performance

TABLE 3

Effect of processparameters on coatning assessed by strikethrough tests.

| Ethanol % | ACD[1] mg/ml | Speed nonwoven m/min | Speed Kiss-roll kHz | Strikethrough score[2] |
|---|---|---|---|---|
| 10.0 | 0.0 | 2.0 | 60 | 5 |
| 10.0 | 0.0 | 2.0 | 25 | 5 |
| 10.0 | 1.0 | 1.5 | 60 | 5 |
| 10.0 | 1.0 | 1.5 | 30 | 5 |
| 10.0 | 1.0 | 1.5 | 10 | 5 |
| 10.0 | 1.0 | 1.0 | 60 | 5 |
| 10.0 | 1.0 | 0.5 | 60 | 5 |
| 10.0 | 2.0 | 2.0 | 60 | 5 |
| 10.0 | 2.0 | 1.0 | 60 | 5 |
| 10.0 | 2.0 | 0.5 | 60 | 5 |
| 10.0 | 2.0 | 0.5 | 20 | 5 |
| 96.0 | 0.0 | 2.0 | 60 | 5 |
| 96.0 | 0.0 | 2.0 | 20 | 5 |
| 96.0 | 1.0 | 2.0 | 60 | 2 |
| 96.0 | 1.0 | 4.0 | 60 | 3 |
| 96.0 | 1.0 | 2.0 | 20 | 4 |
| 96.0 | 1.0 | 1.0 | 60 | 2 |
| 96.0 | 1.0 | 0.5 | 60 | 1 |
| 96.0 | 1.0 | 0.5 | 20 | 1 |

[1]C4 modified β-CD, DS from 6-12.
[2]1—excellent performance, 5—very poor performance

TABLE 4

Lab-scale coatning of polypropylene nonwoven.
Nonwoven submerged in solutions for 3-7 sec. and dryes prior to strikethrough tests.

| Ethanol % | ACD[1] mg/ml | Degree of coatning % weight increase | Strikethrough score[2] |
|---|---|---|---|
| 96 | 3 | 2.70 | 2 |
| 96 | 3 | 3.27 | 1 |
| 96 | 3 | 3.10 | 1 |
| 50 | 3 | 5.19 | 1 |
| 50 | 3 | 5.08 | 1 |
| 50 | 3 | 7.33 | 1 |
| 90 | 3 | 3.38 | 1 |
| 90 | 3 | 2.42 | 4 |
| 90 | 3 | 2.48 | 1 |
| 50 | 10 | 19.99 | 2 |
| 50 | 10 | 22.23 | 1 |
| 50 | 10 | 30.29 | 1 |

[1]C6 modified β-CD, DS from 6-12.
[2]1—excellent performance, 5—very poor performance

The invention claimed is:

1. A functionalized solid material having a surface that comprises at least 0.003 g/m$^2$ of one or more modified self assembling or self aggregating cyclodextrins in a multilayer,
    wherein at least one of the hydroxyl groups (—OH) of said cyclodextrin is modified to —O—(CO)nR1, —NR1R2, —SR1, —N—COR1, or —O—(CO)nOR1,
    wherein n is an integer from 0 to 1, and
    wherein R1, and R2 are independently of one another straight or branched aliphatic chains of 2-20 carbons.

2. The functionalized solid material according to claim 1, wherein the hydrophilic-lipophilic balance (HLB) of the at least one modified self assembling or self aggregating cyclodextrin is in the range of 3-18.

3. The functionalized solid material according to claim 1, wherein the surface of the solid material contains at least 0.01 g/m$^2$ of one or more modified self assembling cyclodextrins,
    wherein at least one of the hydroxyl groups (—OH) of said cyclodextrin is modified to —O—(CO)nR, and
    wherein R is a straight or branched aliphatic chain of 1-20 carbons and n is an integer from 0 to 1.

4. The functionalized solid material according to claim 1, wherein the at least one modified hydroxyl group is a primary hydroxyl group.

5. The functionalized solid material according to claim 1, wherein the at least one modified hydroxyl group is a secondary hydroxyl group.

6. The functionalized solid material according to claim 1, wherein said solid material is a textile.

7. The functionalized solid material according to claim 1, wherein at least 5% of the modified self assembling or self aggregating cyclodextrins are complexed with at least one guest molecule.

8. The functionalized solid material according to claim 1, wherein R1, and R2 are independently of one another straight or branched aliphatic chains of 4-12 carbons.

9. The functionalized solid material according to claim 1, wherein R1 and R2 are independently of one another straight or branched aliphatic chains of 4-8 carbons.

* * * * *